US00PP17501P2

(12) United States Plant Patent
Leth

(10) Patent No.: US PP17,501 P2
(45) Date of Patent: Mar. 13, 2007

(54) ***OTACANTHUS* PLANT NAMED 'CALANDA'**

(50) Latin Name: *Otacanthus azureus Ronse.*
Varietal Denomination: Calanda

(75) Inventor: Carsten Leth, Odense (DK)

(73) Assignee: Ex-Plant A/S, Odense (DK)

( * ) Notice: Subject to any disclaimer, the term of this patent is extended or adjusted under 35 U.S.C. 154(b) by 0 days.

(21) Appl. No.: 11/235,272

(22) Filed: Sep. 27, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Louanne Krawczewicz Myers
(74) *Attorney, Agent, or Firm*—Foley & Lardner LLP

(57) ABSTRACT

A new distinct cultivar of *Otacanthus* plant named 'Calanda', characterized by its compact plant habit; dense and bushy plant form, mainly due to upright stems; deep violet colored corolla (RHS N88A) and a white throat spot; and less need for chemical growth retardation, due to plant having shorter internodes, shorter branches and shorter plant height.

5 Drawing Sheets

Botanical designation: *Otacanthus azureus Ronse.*
Variety denomination: 'Calanda'.

BACKGROUND OF THE INVENTION

The present Invention relates to a new and distinct cultivar of *Otacanthus* plant of the *Schrophulariaceae* family, botanically known as *Otacanthus azureus Ronse.,* syn. *O. caeruleus Lindl.,* commonly known by the name Brazilian Snapdragon, and hereinafter referred to by the name 'Calandra'.

The new *Octacanthus* is a product of a planned breeding program conducted by the Inventor, Carsten Leth, in Stige, Denmark. The new *Otacanthus* originated from a selfing made in 2002 by the Inventor of an unnamed, unpatented seedling plant of an *Otacanthus azureus Ronse.* cultivar designated '2015', which was a selection from a seedling batch produced from wild type plants. The Inventor selected the new *Otacanthus* cultivar as a single flowering plant from the progeny of the above selfing in April of 2003 on the basis of its flower color combination, freely branching habit, and upright, compact plant habit. Plants of the new *Otacanthus* cultivar 'Calanda' have upright, compact plant habit, are freely branching, and produce flowers with unique blue colored petals.

Asexual reproduction of the new cultivar was first performed in October of 2003 by terminal cuttings taken and propagated and trial production batches in Stige, Denmark, has demonstrated that the combination of unique features as disclosed herein for this new *Otacanthus* cultivar are firmly fixed and retained through successive generations of asexual reproduction. The new cultivar reproduces true-to-type.

BRIEF SUMMARY OF THE INVENTION

The following traits have been repeatedly observed and are determined to be the unique characteristics of 'Calanda'. These characteristics in combination distinguish 'Calanda' as a new and distinct cultivar:

1. Compact plant habit;
2. Dense and bushy plant form, mainly due to upright stems;

3. Deep violet colored corolla (RHS N88A) and a white throat spot; and
4. Less need for chemical growth retardation, due to plant having shorter internodes, shorter branches and shorter plant height.

Plants of the cultivar 'Calanda' can be compared to plants of the *Otacanthus azureus Ronse.* cultivar designated 'Clone B' (unpatented). 'Clone B' was selected from the same seedling production batch of wild type plants that the *Otacanthus azureus Ronse.* seedling plant designated '2015' was selected. In side-by-side comparisons conducted by the Inventor in Stige, Denmark, plants of the new cultivar 'Calanda' and the comparison cultivar 'Clone B' differ in the following characteristics:

1. Plants of 'Calanda' are shorter in height (about 25 cm) than plants of 'Clone B' (about 35 cm);
2. Plants of 'Calanda' have shorter and sturdier lateral branches (about 15 cm in length) than plants of 'Clone B' (about 18 cm in length);
3. Plants of 'Calanda' have shorter and sturdier internodes (about 2–3 cm in length, after treated with growth retardant) than plants of 'Clone B' (about 4–5 cm in length); and
4. Plants of 'Calanda' have a larger inflorescence height (about 8 to 9 cm) than plants of 'Clone B' (about 6 to 7 cm).

BRIEF DESCRIPTION OF THE PHOTOGRAPHS

The accompanying color photographs illustrate the overall appearance and details of flower form, color and structures of the new *Otacanthus* cultivar 'Calanda', showing the colors as true as it is reasonably possible to obtain in color reproductions of this type. Colors in the photographs may differ slightly from the color values cited in the detailed botanical description, which more accurately describe the actual colors of the 'Calanda'.

DETAILED BOTANICAL DESCRIPTION

Figure 1:
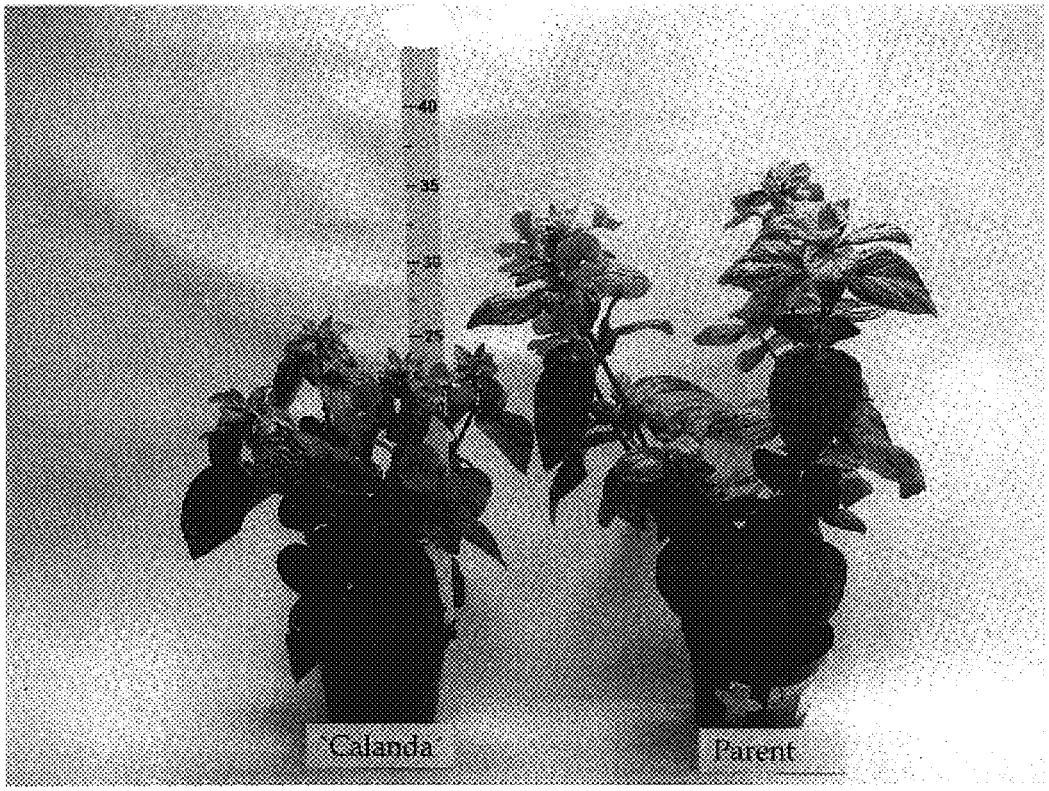
FIG. 1 shows a side view perspective comparing a typical, potted flowering plant of the new cultivar 'Calanda' (on the left) to a typical, potted flowering plant of the cultivar designated '2015' (labelled as "parent" on the right), both grown in 11 cm pots.
Figure 2:
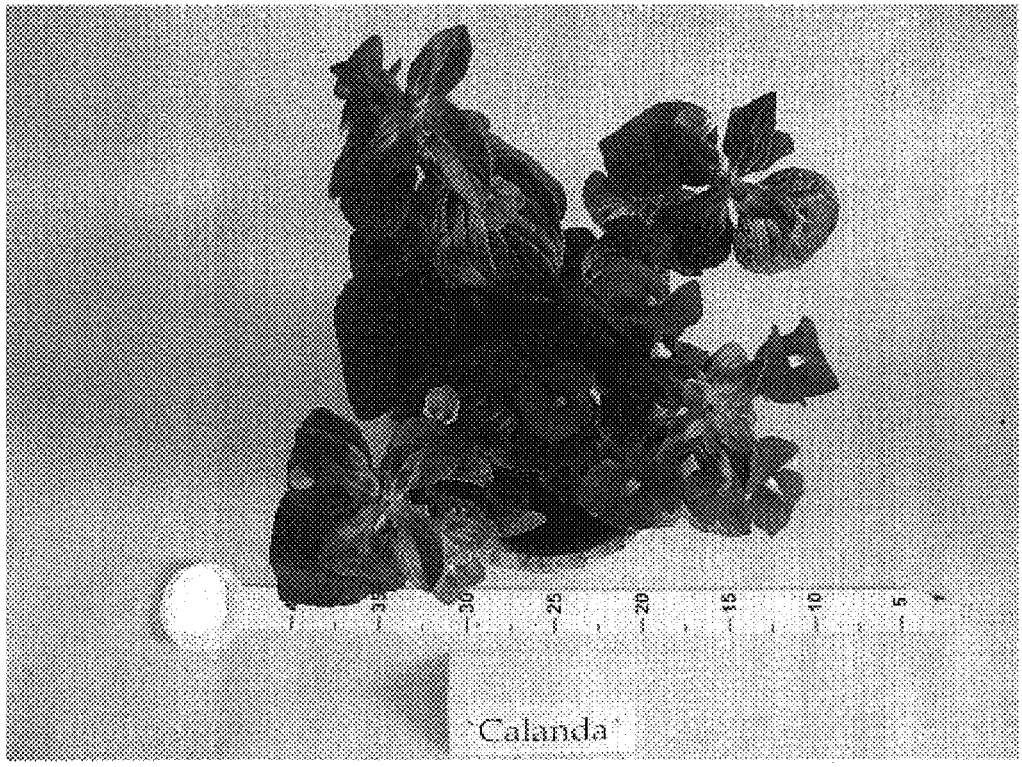
FIG. 2 shows a top view perspective comparing a typical, potted flowering plant of the new cultivar 'Calanda' (on the top) to a typical, potted flowering plant of the cultivar designated '2015' (labelled as "parent" on the bottom), both grown in 11 cm pots.
Figure 2:
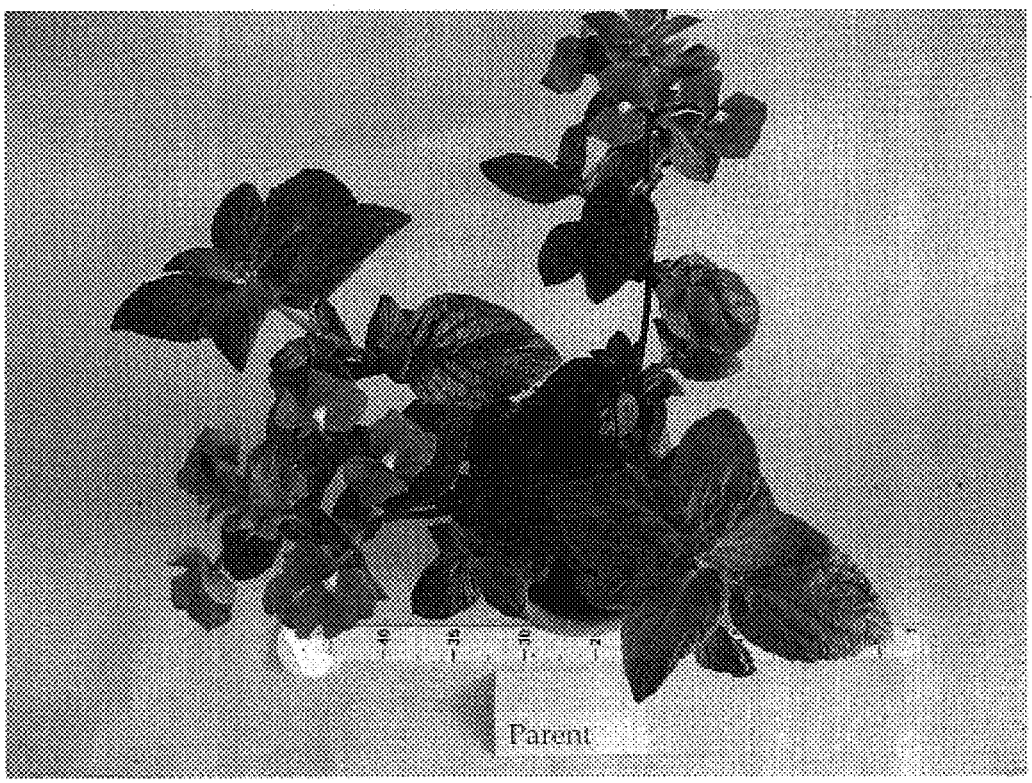
Figure 3:
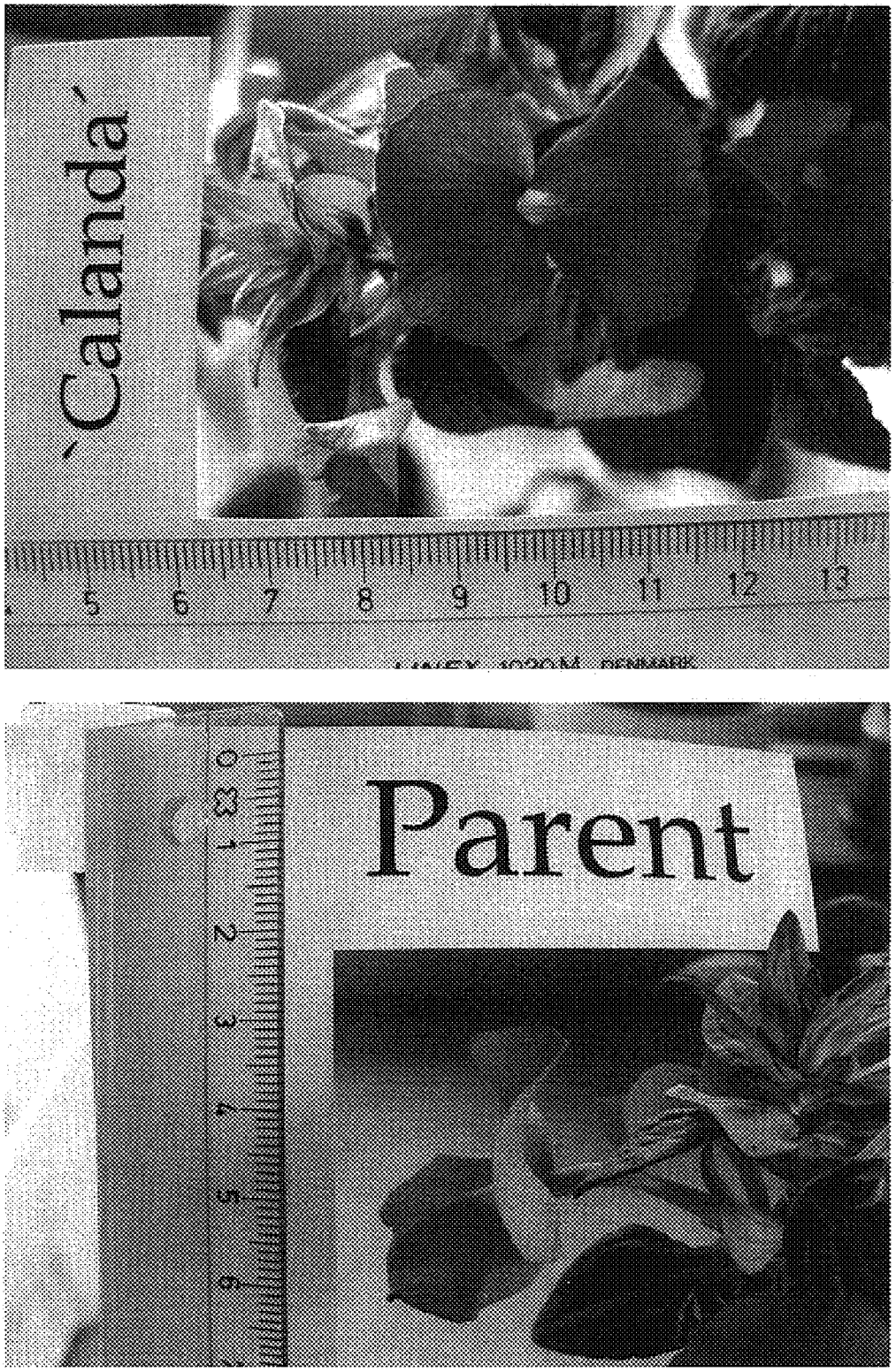
FIG. 3 shows a close-up view comparing the typical leaves and flowers of a typical, potted flowering plant of the new cultivar 'Calanda' (on the top) to the typical flowers and leaves of a typical, potted flowering plant of the cultivar designated '2015' (labelled as "parent" on the bottom), both grown in 11 cm pots.
Figure 4:
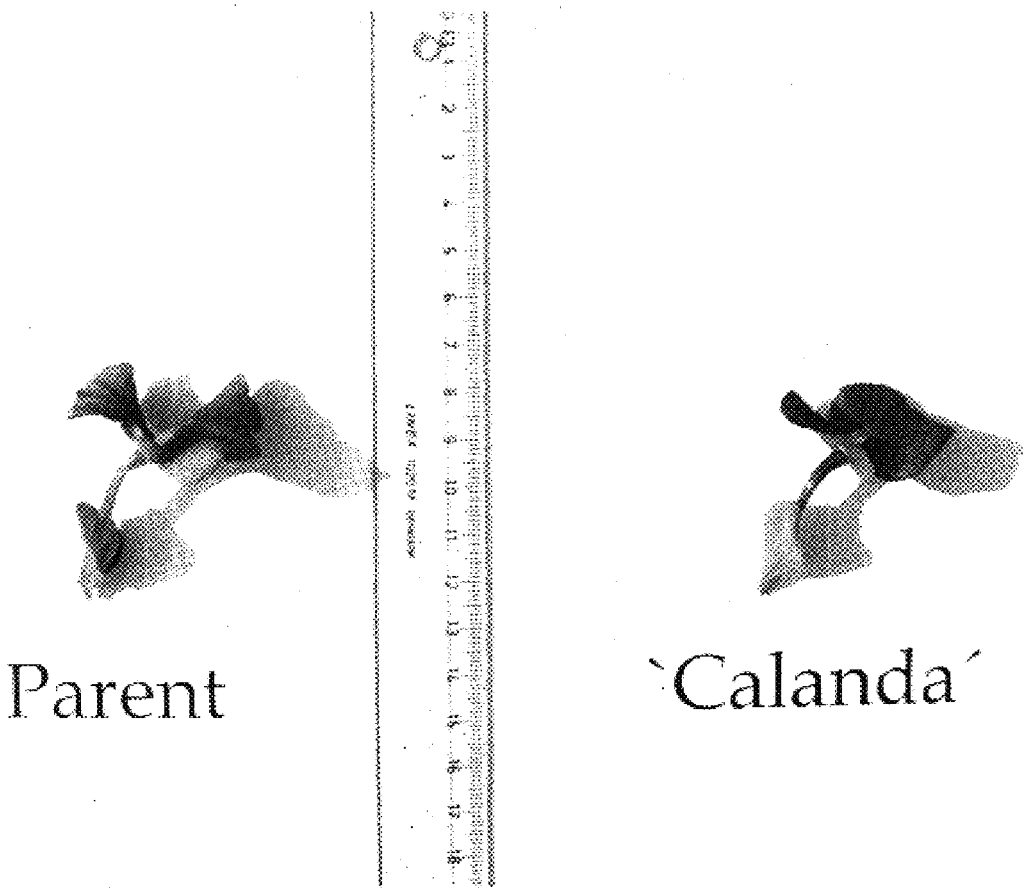
FIG. 4 shows a close-up view comparing a flower produced by a typical, potted flowering plant of the cultivar designated '2015' (labelled as "parent" on the left) to a flower produced by a typical, potted flowering plant of the new cultivar 'Calanda' (on the right).
Figure 5:
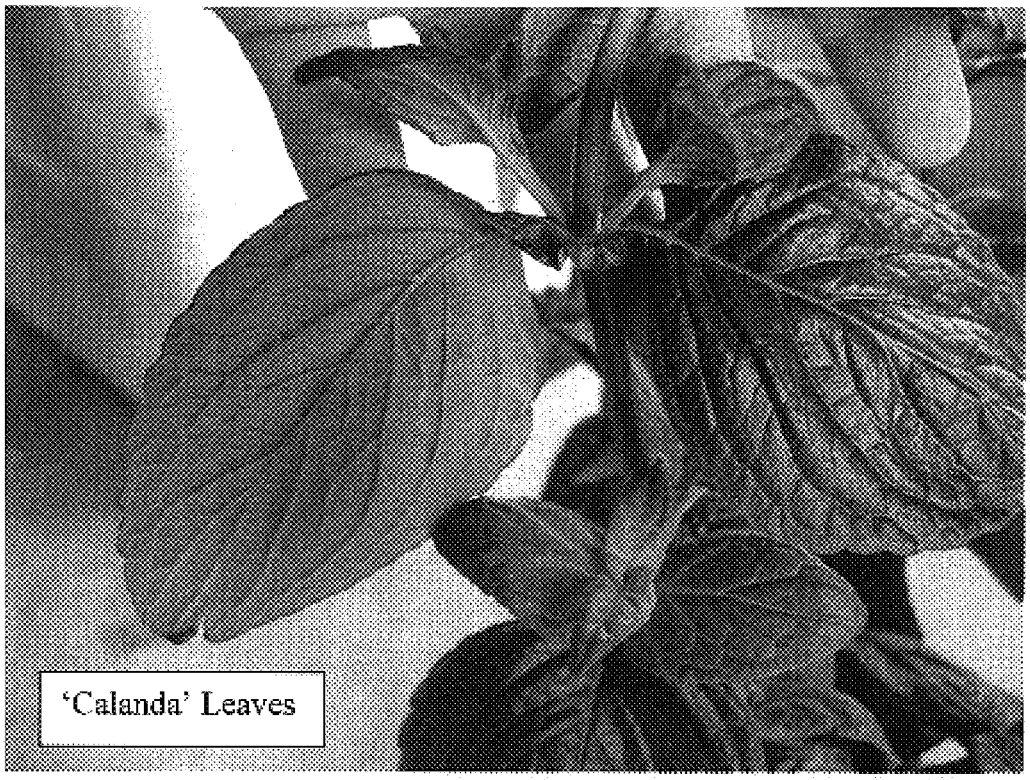
FIG. 5 shows a close-up view of different sizes of leaves (on the top) and different leaves and a bud (on the bottom) produced by a typical flowering plant of the new cultivar 'Calanda'.
Figure 5:
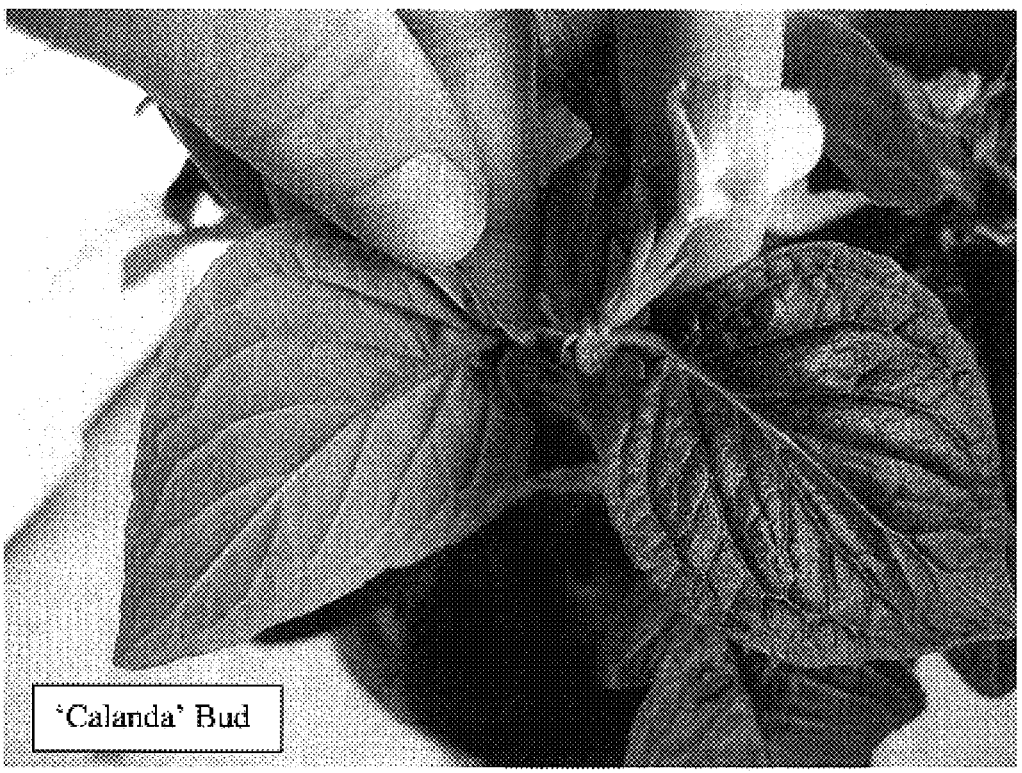

Plants of the new cultivar 'Calanda' have not been observed under all possible environmental conditions. The phenotype may vary somewhat with variations in environment such as temperature, light intensity, day length, and fertility level without, however, any variance in genotype.

The aforementioned photographs, together with the following observations, measurements and values describe plants of the new cultivar 'Calanda' as grown in a glass greenhouse in Stige, Denmark, under conditions which closely approximate those generally used in commercial practice. Plants of 'Calanda' were grown in a greenhouse with the day temperature range of 18° C. to 22° C. and the night temperature range of 16° C. to 18° C. Plants of 'Calanda' were grown in ambient light of +300 $W.m^{-2}$ installed and no photoperiodic treatments were used. Plants of 'Calanda' were treated with the following two growth retardants: 1) a spray of 3 times 0.1% Daminozide during the cutting stage, and 2) 3 times 0.05% Chlormequat after potting.

Color references are made to The Royal Horticultural Society Colour Chart (R.H.S.), $4^{th}$ edition, except where general terms of ordinary dictionary significance are used. Plants used for this description were grown for about 20 weeks after cutting and produced in 11 cm pots. Other pot sizes can be used and the plants are typically intended for outdoor use as a potted or bedding plant in temperate climates while it is perennial plant in tropical areas, such as its native land of Brazil.

Botanical classification: *Otacanthus azureus Ronse.*

Parentage: Selfing of *Otacanthus azureus Ronse.* seedling plant designated '2015', which was a selection from a seedling batch produced from wild type plants.

Propagation:

*Type cutting.*—Terminal vegetative cuttings taken from non-flowering plants.

*Time to initiate roots.*—About 10 to 14 days at 18° to 21° C. in tunnels in a greenhouse.

*Root description.*—Fine, fibrous, well branched.

Plant description:

*Form.*—Perennial, but produced as an annual plant, with upright, globular to cylindrical plant habit. 'Calanda' flowers in terminal spikes. Freely branching, branches forming at every node; dense and bushy.

*Crop time.*—After rooting, about 16 weeks are required to produce finished flowering plants in 11 cm pots.

*Vigor.*—Moderately vigorous growth rate.

*Plant size.*—Height (soil level to top of plant plane): About 25 cm, Range of 20–35 cm. Width: About 20 cm, Range about 18–25 cm.

*Lateral branches.*—Freely branching with about 6 lateral flowering branches forming at every node; dense and bushy. Lateral branches measure about 15 cm in length and about 3 to 4 mm in diameter. Internode length measures about 2 to 3 cm (after treatment with growth retardant). Lateral branch color is RHS 137B, green. About 6 buds per lateral branch and about 6 to 8 flowers per lateral branch.

*Stems.*—Stems are strong in strength, quadrangular in shape, with an upright aspect, with glandular hairs pubescence and glutinous, green in color, RHS 137B, and have mint-like scent. Stems measure about 4 cm in length and about 5 mm in diameter.

*Foliage description.*—Leaves opposite, single, elliptic in shape, finely serrate margin, pinnate venation, winged petioles and mint-like scent. Length: About 3 to 6 cm. Width: About 35 mm Apex: Acuminate to Acute. Base: Cuneate. Texture (both upper and lower sides): Rough, buckled, with glandular hairs on underside and glutinous. Color: Young foliage: (upper side and under side): Green, RHS 137C. Mature foliage: (upper side and under side): Green, RHS 137B. Venation pattern: Pinnate. Venation color: (upper side): Green, RHS 137B; (under side): Green, RHS 137A. Petiole length: Up to 4 cm. Petiole diameter: 2 to 3 mm. Petiole color: Green, RHS 137B.

Flower description:

*Flower arrangement and shape.*—Bilabiate flowers in tight, terminal spikes.

*Natural flowering season.*—Continuous in tropical regions, such as native land Brazil, and as produced cultivar, spring and summer. In colder climates, season can be extended by greenhouse production with high temperatures.

*Time to flower (after potting).*—About 11 weeks.

*Flower longevity on the plant.*—About 2 to 3 weeks. However, longevity of individual flowers is highly dependent on temperature and light conditions. Flowers persistent, petals folding and withering slowly to greenish-white color, RHS 157C.

*Flower longevity as a cut flower.*—Not tested.

*Self-cleaning.*—Yes.

*Quantity of buds and flowers per plant.*—About 120 to 140.

*Rate of flower opening.*—About 1 every other day per stem.

*Fragrance.*—Mint.

*Inflorescence size.*—Diameter: About 7 cm. Height: About 9 cm.

*Buds.*—Lanceolate shape, measures about 20 mm in length (before anthesis) and about 5 mm in diameter, color: green, RHS 143D.

*Flowers.*—Shape is hypocrateriform/salverform, bilabiate corolla, with basal tube. Aspect upright to outward. Lips cordate to reniform; rounded tips and fused base. Entire margin; lower anterior lip slightly lobed. Corolla lips about 35 mm in diameter, range 30 to 40 mm; about 40 mm in height, range 35 to 45 mm; tube length about 38 mm and tube width about 10 mm. Texture (both upper and lower sides) is silky, papillose; underside is less papillose. Color when opening: (upper side): corolla lips violet, RHS N88A, and tube and throat, light gray (green-white), RHS 157C; (under side): corolla lips violet, RHS N88C. Color fully opened: (upper side): corolla lips violet, RHS N88B and throat with white spot, RHS 155A; (under side): corolla lips violet, RHS N88A. Color fades to light gray (green-white) RHS 157C. Throat length about 40 mm and width about 10 mm. Throat texture is glabrous. Primary outside color of throat is violet, RHS N88B fading to RHS N88D at base. No true palate, but the bases of the two lips almost close the entrance to the throat by being buckled.

*Calyx.*—Imbricate, 5 sepals, glabrous, length about 12 to 13 mm, diameter of fused part about 5 mm.

*Sepals.*—Lanceolate in shape, acute tip and fused base; dorsal sepal ovate. Glabrous and glandular texture (both upper and lower sides). Entire margin. Length about 12 to 13 mm; width about 2 mm. Color when opening: (upper side): green, RHS 137D; (under side): green, RHS 137C. Color fully opened: (upper side): green, RHS 137C; (under side): green, RHS 137B.

*Peduncles.*—Length measuring about 3 to 4 cm, diameter measuring about 3 to 4 mm, angle about 10°, moderately strong in strength, color: green, RHS 137B.

*Pedicel.*—Length measuring from 1 to 2 mm, diameter measuring about 2 to 3 mm, angle about 40° to 60°, strong in strength, color: green, RHS 137C.

Reproductive organs:

*Androecium.*—Stamen: 4, didynamous, included. Anthers: Double reniform, connate, measuring about 1 to 2 mm, not protruding, with filaments measuring about 20 to 22 mm, white color, RHS 155D. Pollen: Average amount (2 sterile and 2 fertile anthers), color: white, RHS 155B.

*Gynoecium.*—Pistil: One, 25 to 30 mm in length. Stigma: Bilobed in shape, color: white, RHS 155B. Style: Length: about 20 mm, color: white, RHS 155B. Ovary: Light green, RHS 137D.

*Seed.*—Many reticulate, caruncled seeds measuring about 0.6 in length and 0.3 mm in diameter, and with brown color, RHS 200B.

*Fruit.*—None observed.

Weather tolerance: Plants of the new *Otacanthus* cultivar have exhibited good tolerance to draught, rain and wind. Low temperature tolerance to −1° C. and high temperature tolerance to +40° C.

Pest/disease resistance/susceptibility: No particular diseases or pests observed.

I claim:

1. A new and distinct cultivar of *Otacanthus* plant named 'Calanda', as illustrated and described herein.

* * * * *